US011020470B2

(12) United States Patent
Wen et al.

(10) Patent No.: US 11,020,470 B2
(45) Date of Patent: Jun. 1, 2021

(54) VIRUS-LIKE PARTICLES

(71) Applicant: THE REGENTS OF THE UNIVERSITY OF MICHIGAN, Ann Arbor, MI (US)

(72) Inventors: Fei Wen, Ann Arbor, MI (US); Eshita Khera, Ann Arbor, MI (US); Brett Dallas Hill, Ann Arbor, MI (US); Syed Rizvi, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/566,069

(22) PCT Filed: Apr. 12, 2016

(86) PCT No.: PCT/US2016/027117
§ 371 (c)(1),
(2) Date: Oct. 12, 2017

(87) PCT Pub. No.: WO2016/168187
PCT Pub. Date: Oct. 20, 2016

(65) Prior Publication Data
US 2018/0133303 A1    May 17, 2018

Related U.S. Application Data

(60) Provisional application No. 62/146,605, filed on Apr. 13, 2015.

(51) Int. Cl.
| | |
|---|---|
| *A61K 39/12* | (2006.01) |
| *C12N 15/81* | (2006.01) |
| *A61K 39/145* | (2006.01) |
| *A61K 39/21* | (2006.01) |
| *C07K 14/395* | (2006.01) |
| *A61K 39/00* | (2006.01) |

(52) U.S. Cl.
CPC ............ *A61K 39/12* (2013.01); *A61K 39/145* (2013.01); *A61K 39/21* (2013.01); *C12N 15/81* (2013.01); *A61K 2039/5258* (2013.01); *A61K 2039/70* (2013.01); *C07K 14/395* (2013.01); *C12N 2740/16023* (2013.01); *C12N 2740/16034* (2013.01); *C12N 2760/14123* (2013.01); *C12N 2760/14134* (2013.01); *C12N 2760/16123* (2013.01); *C12N 2760/16134* (2013.01); *C12N 2760/16223* (2013.01); *C12N 2800/102* (2013.01)

(58) Field of Classification Search
None
See application file for complete search history.

(56) References Cited

U.S. PATENT DOCUMENTS

| | | | |
|---|---|---|---|
| 2004/0009193 A1 | 1/2004 | Morikawa | |
| 2008/0003239 A1* | 1/2008 | Duke | A61K 39/145 424/206.1 |
| 2013/0101617 A1* | 4/2013 | Binley | A61K 39/21 424/196.11 |
| 2013/0243808 A1 | 9/2013 | Baer | |
| 2014/0220061 A1* | 8/2014 | Evans | A61K 39/12 424/186.1 |
| 2018/0133303 A1* | 5/2018 | Wen | A61K 39/12 |

FOREIGN PATENT DOCUMENTS

| | | |
|---|---|---|
| CA | 2418091 | 2/2002 |
| WO | WO 2006/045532 | 5/2006 |
| WO | WO 2010/003225 | 1/2010 |

OTHER PUBLICATIONS

Akahata et al., A virus-like particle vaccine for epidemic Chikungunya virus protects nonhuman primates against infection. Nat Med. Mar. 2010;16(3):334-8.
Hill et al., Production and Characterization of Influenza Virus-like Particles in *Saccharomyces cerevisiae*. Poster. Presented at Blue/Green Seminar, Michigan State University. Nov. 6, 2014. 1 Page.
Sakuragi et al., HIV type 1 Gag virus-like particle budding from spheroplasts of *Saccharomyces cerevisiae*. Proc Natl Acad Sci U S A. Jun. 11, 2002;99(12):7956-61.
International Search Report and Written Opinion for PCT/US2016/027117, dated Sep. 8, 2016, 11 pages.

* cited by examiner

*Primary Examiner* — Shanon A. Foley
(74) *Attorney, Agent, or Firm* — Casimir Jones SC; David W. Staple

(57) ABSTRACT

Provided herein are membrane enveloped virus-like particles (VLPs), and methods of use and synthesis thereof. In particular, yeast-cell-derived VLPs are provided that comprise surface-displayed glycoproteins and/or multiple virally-derived proteins.

20 Claims, 8 Drawing Sheets

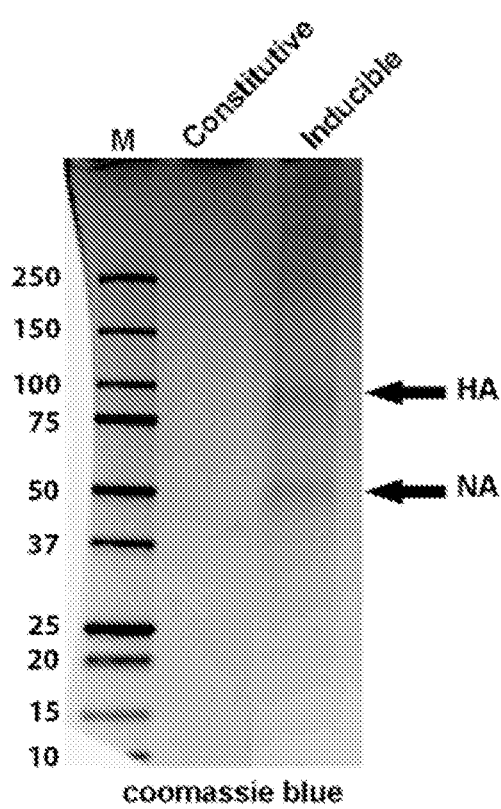
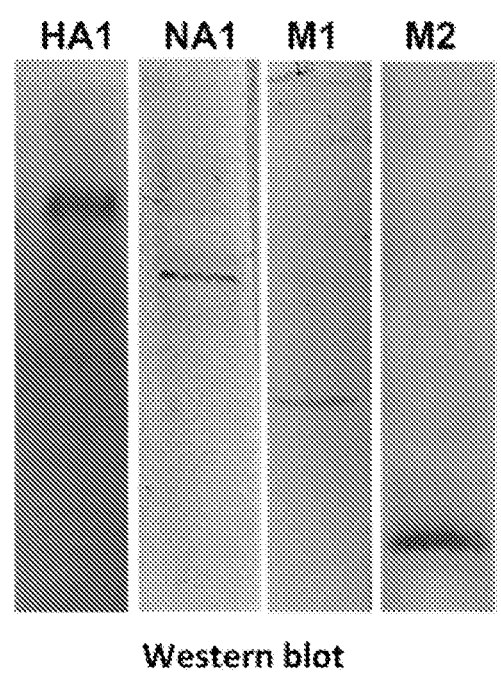
FIG. 1A
FIG. 1B

FIG. 6

VIRUS-LIKE PARTICLES

CROSS REFERENCE TO RELATED APPLICATIONS

The present invention claims the priority benefit of U.S. Provisional Patent Application 62/146,605, filed Apr. 13, 2015, which is incorporated by reference in its entirety.

FIELD

Provided herein are membrane enveloped virus-like particles (eVLPs), and methods of use and synthesis thereof. In particular, yeast-cell-derived eVLPs are provided that comprise surface-displayed glycoproteins and/or multiple virally-derived proteins.

BACKGROUND

Viruses are responsible for many of the most deadly and costly diseases on earth. Due at least in part to the capacity of many viruses to mutate and evade a host's immune system, development of treatments and prophylaxes for viral infections remains a challenge. Accordingly, it is of great importance to develop compositions for the treatment and/or prevention of viral infection, as well as systems and methods for the synthesis thereof.

SUMMARY

Provided herein are membrane enveloped virus-like particles (eVLPs), and methods of use and synthesis thereof. In particular, yeast-cell-derived eVLPs are provided that comprise surface-displayed glycoproteins and/or multiple virally-derived proteins.

In some embodiments, provided herein are enveloped virus-like particles (eVLPs) comprising: (a) a virally-derived internal structural (e.g., matrix, matrix-like, and/or capsid) protein; (b) a virally-derived surface-displayed protein; and (c) a yeast-plasma-membrane-derived envelope. In some embodiments, an assembly of a plurality of said virally-derived internal structural (e.g., matrix, matrix-like, and/or capsid) protein underlies the envelope, and a plurality of the virally-derived surface-displayed proteins are displayed on the envelope on the exterior of the eVLP. In some embodiments, the surface-displayed protein is a glycoprotein. In some embodiments, the yeast-plasma-membrane-derived envelope comprises lipid and fatty acid character consistent with a yeast plasma membrane (e.g., natural yeast plasma membrane). In some embodiments, the yeast-plasma-membrane-derived envelope comprises additional membrane components or ratios of components inconsistent with a yeast plasma membrane (e.g., natural yeast plasma membrane).

In some embodiments, provided herein are influenza enveloped virus-like particles (eVLPs) comprising: (a) an influenza-derived matrix protein; (b) an influenza-derived surface-displayed protein; and (c) a yeast-plasma-membrane-derived envelope. In some embodiments, the influenza-derived matrix protein is selected from influenza M1 and/or M2, or a structural and/or functional variant thereof. In some embodiments, the influenza-derived surface-displayed protein is selected from influenza HA and/or NA, or a structural and/or functional variant thereof. In some embodiments, the plasma membrane comprises lipid and fatty acid character consistent with a yeast plasma membrane (e.g., natural yeast plasma membrane). In some embodiments, the eVLP comprises influenza-derived matrix protein or influenza-derived surface-displayed protein from two or more influenza types and/or strains. In some embodiments, the eVLP comprises influenza HA and/or NA from two or more influenza types and/or strains. In some embodiments, the eVLP comprises one or more of influenza proteins: NP, NS1, NS2, PA, PB1, PB1-F2 and/or PB2. In some embodiments, the influenza eVLP comprises: (a) influenza matrix proteins M1 and M2, or non-natural variants thereof; and (b) influenza surface-displayed proteins HA and NA, or non-natural variants thereof. In some embodiments, the influenza eVLP comprises one or more HA types selected from the group consisting of H1, H2, H3, H4, H5, H6, H7, H8, H9, H10, H11, H12, H13, H14, H15, H16, H17, and H18. In some embodiments, the influenza eVLP comprises one or more NA types selected from the group consisting of N1, N2, N3, N4, N5, N6, N7, N8, and N9.

In some embodiments, provided herein are Ebola enveloped virus-like particles (eVLPs) comprising: (a) an Ebola-derived internal structural protein; (b) an Ebola-derived surface-displayed protein; and (c) a yeast-plasma-membrane-derived envelope. In some embodiments, the Ebola-derived internal structural protein is Ebola VP40, or a non-natural structural and/or functional variant thereof. In some embodiments, the Ebola-derived surface-displayed protein is Ebola GP, or a non-natural structural and/or functional variant thereof. In some embodiments, the plasma membrane comprises lipid and fatty acid character consistent with a yeast plasma membrane. In some embodiments, the Ebola eVLP comprises: (a) Ebola internal structural protein VP40, or non-natural variants thereof; and (b) Ebola surface-displayed protein GP, or non-natural variants thereof. In some embodiments, the Ebola eVLP further comprises VP24. In some embodiments, the Ebola eVLP comprises one or more of VP30, VP35, and NP.

In some embodiments, provided herein are HIV enveloped virus-like particles (eVLPs) comprising: (a) an HIV-derived internal structural protein; (b) an HIV-derived surface-displayed protein; and (c) a yeast-plasma-membrane-derived envelope. In some embodiments, the HIV-derived internal structural protein is Gag or HIV MA, or a non-natural structural and/or functional variant thereof. In some embodiments, the HIV-derived surface-displayed protein is HIV GP160, GP120, and/or GP41, or a non-natural structural and/or functional variant thereof. In some embodiments, the plasma membrane comprises lipid and fatty acid character consistent with a yeast plasma membrane. In some embodiments, the HIV eVLP comprises: (a) HIV matrix protein MA, or non-natural variants thereof and (b) HIV surface-displayed proteins GP120, and GP41, or non-natural variants thereof. In some embodiments, the HIV eVLP further comprises one or more of CA, SP1, NC, SP2, and/or p6.

In some embodiments, provided herein are systems for the production of enveloped virus-like particles (eVLPs) comprising: (a) a yeast cell engineered to express two or more viral proteins; (b) yeast culture media; and (c) a spheroplasting cell wall-digesting enzyme. In some embodiments, the two or more viral proteins comprise a virally-derived internal structural protein (e.g., matrix) and a virally-derived surface-displayed protein. In some embodiments, the two or more viral proteins are expressed in the yeast cell(s). In some embodiments, the two or more viral proteins are encoded by one or more nucleic acids (e.g., vectors) within said yeast cell (e.g., stably, transiently, etc.). In some embodiments, the nucleic acids encoding the two or more viral proteins are integrated into the yeast genome. In some embodiments, the two or more viral proteins are expressed from inducible promoters. In some embodiments, the yeast cell is stably or transiently engineered to express the two or more viral proteins. In some embodiments, the two or more viral proteins are expressed from the same vector. In some embodiments, the two or more viral proteins are expressed from separate vectors. In some embodiments, the two or more viral proteins are expressed from the same type of inducible promoter. In some embodiments, the two or more viral proteins are expressed from different types of inducible promoter. In some embodiments, the two or more viral proteins are derived from the same virus type and strain. In some embodiments, the two or more viral proteins are derived from an enveloped virus. In some embodiments, the two or more viral proteins are derived from an influenza, Ebola, or HIV virus. In some embodiments, the two or more viral proteins are derived from different strains of the same virus type.

In some embodiments, provided herein are methods for the production of an enveloped virus-like particles (eVLPs) comprising: (a) expressing two or more virally-derived proteins in a yeast cell in yeast culture media; (b) exposing the yeast cell to conditions that result in degradation of the yeast cell wall to produce a spheroplast; and (c) allowing budding of an eVLP from the spheroplast. In some embodiments, methods further comprise: (d) purifying the eVLP from the yeast culture media. In some embodiments, purifying comprises one or more of centrifugation, ultracentrifugation, filtration, size-exclusion, affinity purification, etc. In some embodiments, conditions that result in degradation of the yeast cell wall to produce a spheroplast are selected from enzymatic digestion, mechanical rupture, and chemical destabilization. In some embodiments, conditions that result in degradation of the yeast cell wall to produce a spheroplast comprise exposing the yeast cell to a spheroplasting cell wall-digesting enzyme. In some embodiments, the spheroplasting cell wall-digesting enzyme is selected from Zymolase, Lyticase, etc. In some embodiments, the two or more viral proteins comprise a virally-derived internal structural (e.g., matrix) protein and a virally-derived surface-displayed protein. In some embodiments, the two or more viral proteins are expressed from inducible promoters. In some embodiments, the yeast cell is stably or transiently engineered to express the two or more viral proteins. In some embodiments, the two or more viral proteins are expressed from the same vector. In some embodiments, the two or more viral proteins are expressed from separate vectors. In some embodiments, the two or more viral proteins are expressed from the same type of inducible promoter. In some embodiments, the two or more viral proteins are expressed from different types of inducible promoter. In some embodiments, the two or more viral proteins are derived from the same virus type and strain. In some embodiments, the two or more viral proteins are derived from an enveloped virus. In some embodiments, the two or more viral proteins are derived from an influenza, Ebola, or HIV virus. In some embodiments, the two or more viral proteins are derived from different strains of the same virus type.

In some embodiments, provided herein are methods of immunizing a subject against a viral infection comprising administering to the subject an effective dose of an enveloped virus-like particle (eVLP) described herein. In some embodiments, the eVLP displays one or more viral antigens and induces an immune response in the subject against infection by a natural virus also displaying one or more of said viral antigens. In some embodiments, the eVLP displays two or more viral antigens and induces an immune response in the subject against infection by two or more different natural virus, each displaying one or more of said viral antigens.

In some embodiments, provided herein are the eVLPs described herein for use as a medicament. In some embodiments, provided herein are the eVLPs described herein for use in the treatment and/or prevention of viral infection.

BRIEF DESCRIPTION OF THE DRAWINGS

FIG. 1A-B shows (A) Coomassie blue staining, and (B) Western blot of influenza viral proteins expressed in yeast.

FIG. 6 shows transmission electron micrographs depicting EbVLPs produced by the co-expression Ebola proteins GP and VP40. (A) Negative control, (B) Multiple filamentous yeast EbVLP (indicated by arrows) ranging from 600 nm to 3 μm in length and 60-80 nm in diameter, consistent with the dimensions of authentic Ebolavirus. Conformational similarity is observed between (C) yeast EbVLP and (D) mammalian EbVLP (Noda et al, *J Virol.*, 76(10): 4855-4865 (2002); incorporated by reference in its entirety) and (E) the authentic Ebolavirus.

DEFINITIONS

Figure 2:
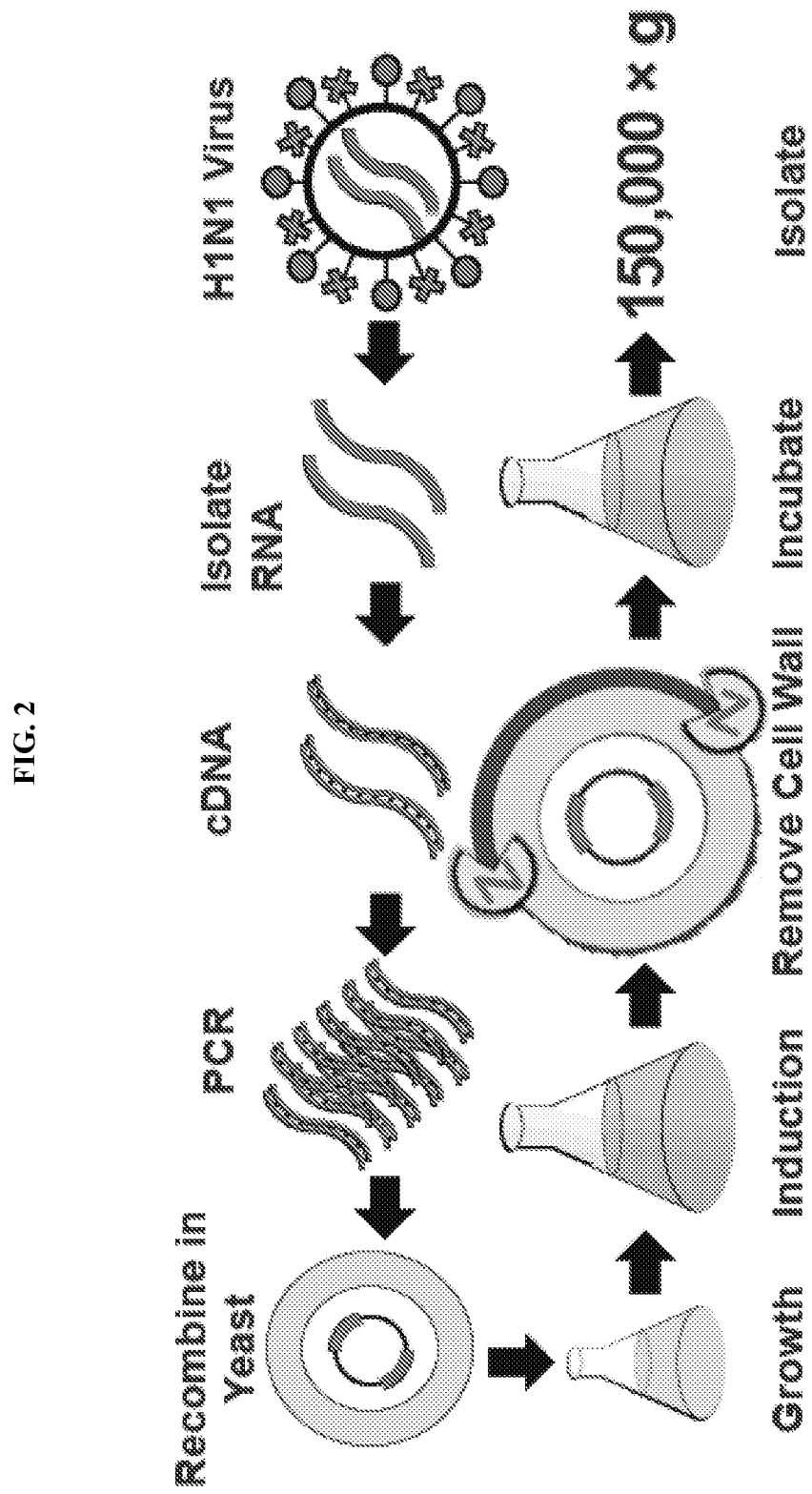
FIG. 2 shows a schematic of an exemplary VLP production method.

As used herein, the term "virus-like particle" (VLP) refers to a non-replicating, multicomponent structure composed of one or more viral proteins or virally-derived peptides or polypeptides, such as, but not limited to capsid, coat, shell, surface and/or envelope proteins, or variant polypeptides derived from these proteins.

As used herein, the term "enveloped virus-like particle" (eVLP) refers to a VLP comprising an external lipid membrane derived, at least partially, from the host (e.g., yeast cell) or system used to generate the VLP. Viral proteins and/or virally-derived peptides or polypeptides may be completely encapsulated by the external lipid membrane, embedded within the membrane, or attached to the exterior surface of the membrane.

As used herein, the term "viral protein" (or "influenza protein," "HIV protein," "Ebola protein," etc.) refers to a protein having sequence identity with a protein that is encoded by and/or is a component of a particular virus. A viral protein may be the most common naturally-occurring variant of a protein (e.g., "wild-type") or may be a less common "natural variant."

As used herein, the terms "virally-derived peptide," "virally-derived polypeptide," or "virally-derived protein" refer to both naturally-occurring viral peptides, polypeptides, or proteins, as well as peptides, polypeptides, or proteins displaying a degree of sequence identity and/or similarity to a viral protein and/or maintaining one or more structural, mechanistic, or antigenic qualities of the viral protein.

As used herein, the terms "internal structural protein" or "viral internal protein" refer to a structural protein expressed by a virus that underlies the lipid envelope of enveloped virus particles. An internal structural protein, as used herein, forms or is involved in forming the structural layer (e.g., "matrix layer") immediately beneath the envelope. Internal structural proteins may include matrix protein (e.g., the matrix proteins found in Influenza, Ebola, and HIV), matrix-like proteins (e.g., the tegument protein found in Herpes), and capsid proteins. As used herein, a "virally-derived internal structural protein" refers to both naturally-occurring viral internal structural proteins as well as synthetic variants of viral proteins that, while not having naturally-occurring sequences, function as internal structural proteins in the eVLPs described herein.

As used herein, the terms "surface protein" and "surface-displayed protein" refer to a polypeptide or protein that is presented on the surface of a virus or VLP. Viral surface proteins are commonly, but not necessarily, glycoproteins. A surface-displayed protein may be a transmembrane protein with a surface-displayed portion, or a protein that is tethered to the surface of the viral particle (or virus-like particle), for example, being tethered to a transmembrane protein. In some embodiments, a transmembrane protein spans the entire thickness of the plasma membrane. As used herein, a "virally-derived surface protein" refers to both naturally-occurring viral surface proteins as well as synthetic variants of viral surface proteins that, while not having naturally occurring sequences, function as surface-displayed proteins in the eVLPs described herein.

As used herein, the term "subject" broadly refers to any animal, including but not limited to, human and non-human mammals (e.g., primates, rodents, dogs, cats, cows, horses, sheep, etc.). As used herein, the term "patient" typically refers to a subject that is being treated for a disease or condition (e.g., viral infection, etc.) or receiving prophylaxis against viral infection.

As used herein, an "immune response" refers to the action of cells of the immune system (e.g., T lymphocytes, B lymphocytes, natural killer (NK) cells, macrophages, eosinophils, mast cells, dendritic cells, neutrophils, etc.) and macromolecules (e.g., including antibodies, cytokines, etc.) that results in selective targeting, binding to, damage to, destruction of, and/or elimination from a subject of invading pathogens, cells or tissues infected with pathogens, or cancerous or other abnormal cells.

As used herein, the term "immunotherapy" refers to the treatment or prevention of a disease or condition by a method comprising inducing, enhancing, suppressing or otherwise modifying an immune response.

As used herein, "potentiating an immune response" refers to inducing an immune response or increasing the effectiveness or potency of an existing immune response in a subject. This may be achieved by providing antigens in a structure or complex that is readily recognizable and capable of inducing an immune response, by overcoming mechanisms that suppress the host immune response, and/or by stimulating mechanisms that enhance the host immune response.

As used herein, the term "antibody" refers to a whole antibody molecule or a fragment thereof (e.g., Fab, Fab', F(ab')2, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety); it may be a polyclonal or monoclonal antibody, chimeric, a humanized, etc.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7 M^{-1}$, $>10^8 M^{-1}$, $>10^9 M^{-1}$, $>10^{10} M^{-1}$, $>10^{11} M^{-1}$, $>10^{12} M^{-1}$, $>10^{13} M^{-1}$, etc.). In certain such embodiments, an antibody is capable of binding different antigens so long as the different antigens comprise that particular epitope. In certain instances, for example, homologous proteins from different species may comprise the same epitope.

The term "epitope" refers to any polypeptide determinant capable of specifically binding to an immunoglobulin or a T-cell or B-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics. An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "wild-type," refers to a gene or gene product (e.g., protein) that has the characteristics (e.g., sequence) of that gene or gene product isolated from a naturally occurring source, and is most frequently observed in a population. In contrast, the term "mutant" refers to a gene or gene product that displays modifications in sequence when compared to the wild-type gene or gene product. It is noted that "naturally-occurring mutants" are genes or gene products that occur in nature, but have altered sequences when compared to the wild-type gene or gene product; they are not the most commonly occurring sequence. "Synthetic mutants" are genes or gene products that have altered sequences when compared to the wild-type gene or gene product and do not occur in nature. Mutant genes or gene products may be naturally occurring sequences that are present in nature, but not the most common variant of the gene or gene product, or "synthetic," produced by human or experimental intervention.

A "conservative" amino acid substitution refers to the substitution of an amino acid in a polypeptide with another amino acid having similar properties, such as size or charge.

In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic: Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

As used herein, the term "percent sequence identity" refers to the degree (e.g., 50%, 60%, 70%, 80%, 90%, 95%, 98%, 99%, etc.) to which two polymer sequences (e.g., peptide, polypeptide, nucleic acid, etc.) have the same sequential composition of monomer subunits. If two polymers have identical sequences (e.g., 100% sequence identity) they may be referred to herein as having "sequence identity." The term "percent sequence similarity" refers to the degree (e.g., 50%, 60%, 70%, 80%, 90%, 95%, 98%, 99%, etc.) with which two polymer sequences (e.g., peptide, polypeptide, nucleic acid, etc.) have similar polymer sequences. For example, similar amino acids are those that share the same biophysical characteristics and can be grouped into the families (see above). If two polymers have sequences that have monomers at each position that share the same biophysical characteristics they may be referred to herein as having "sequence similarity." The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

The term "effective dose" or "effective amount" refers to an amount of an agent, e.g., a VLP, that results in a desired biological outcome (e.g., potentiation of viral immunity).

As used herein, the terms "administration" and "administering" refer to the act of providing a therapeutic, prophylactic, or other agent to a subject for the treatment or prevention of one or more diseases or conditions. Exemplary routes of administration to the human body are through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition as well as individuals who are at risk of acquiring a particular condition or disorder (e.g., genetic or epigenetic predisposition, geography, lifestyle, age, gender, etc.). The term "treating" refers to administering an agent to a subject for therapeutic and/or prophylactic/preventative purposes.

As used herein, the terms "co-administration" and "co-administering" refer to the administration of at least two agent(s) or therapies to a subject (e.g., a VLP and one or more additional antiviral or immunotherapeutic agents). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent (e.g., binding agent) with a carrier, inert or active, making the composition especially suitable for diagnostic or therapeutic use in vitro, in vivo or ex vivo.

The term "pharmaceutically acceptable" as used herein, refers to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, a "diagnostic" or "diagnostic test" includes the detection, identification, or characterization of a disease state or condition of a subject (e.g., viral infection).

DETAILED DESCRIPTION

Provided herein are membrane enveloped virus-like particles (VLPs), and methods of use and synthesis thereof. In particular, yeast-cell-derived VLPs are provided that comprise surface-displayed glycoproteins and/or multiple virally-derived proteins.

Provided herein are systems and methods for the production of enveloped virus-like virus particles (eVLPs) in, for example, yeast cells. In some embodiments, the eVLPs comprise viral proteins (or virally-derived polypeptides) self-assembled into a complex that structurally resembles a virus (e.g., comprises capsid, matrix, and/or other structural proteins; adopts a virus-like geometry, displays viral antigens, is recognized by host immune system, etc.). In some embodiments, an eVLP mimics (e.g., structurally, antigenically, etc.) one or more viruses when administered to a subject (e.g., elicits immune response), but is not capable of replication and/or cell infection (e.g., lacks genetic material). In some embodiments, an eVLP adopts a geometry (e.g., size and shape) that mimics that of a virus (e.g., filamentous, icosahedral, spherical, etc.). In some embodiments, the eVLP induces an immune response to one or more viruses it is intended to mimic (e.g., the one or more viruses for which it displays antigenic viral proteins or virally-derived polypeptides), when administered to a subject.

Production System

In some embodiments, systems are provided for producing (e.g., expressing, assembling, budding, etc.) viral or virally-derived components (e.g., expressing viral or virally-derived proteins) and generating VLPs (e.g., eVLPs). Suitable systems may be cellular (e.g., yeast cells), non-cellular, or cell lysate expression systems. In some embodiments, viral or virally-derived proteins are expressed within a lipid bilayer, under conditions such that VLPs comprising the viral or virally-derived proteins bud off of the lipid bilayer.

In some embodiments, viral or virally-derived proteins are expressed in a cell comprising a lipid bilayer contained within a cell wall (e.g., bacteria, yeast, plant, etc.). In some embodiments, upon degradation of the cell wall (e.g., physically, by addition of an agent, etc.) to generate a spheroplast, budding of eVLPs from the lipid bilayer is induced.

In some embodiments, non-cellular systems that mimic the lipid bilayer and cell wall described above are used in an analogous technique to generate eVLPs.

In some embodiments, viral or virally-derived proteins are expressed in yeast cells (e.g., comprising a lipid bilayer contained within a cell wall). In some embodiments, upon degradation of the cell wall (e.g., physically, by addition of an agent, etc.) to generate a spheroplast, budding of eVLPs from the lipid bilayer is induced. In some embodiments, any suitable species of strain of yeast finds use as an expression and VLP-production system. Suitable yeasts include, but are not limited to: *Pichia pastoris, Saccharomyces cerevisiae, Arxula adeninivorans* (*Blastobotrys adeninivorans*), *Candida boidinii, Hansenula polymorpha* (*Pichia angusta*), *Kluyveromyces lactis, Yarrowia lipolytica*, etc.

In some embodiments, viral or virally-derived proteins are expressed in a yeast expression system (e.g., yeast cell line) under a constitutive promoter, inducible promoter, or a combination thereof. In some embodiments, viral or virally-derived proteins are expressed in a yeast expression system (e.g., yeast cell line) under the control of an inducible promoter. In some embodiments, suitable inducible promoters include, but are not limited to: GAL1, GAL7, GAL10, Met25, CUP1, etc. In some embodiments, multiple viral or virally-derived proteins are expressed on the same vector. In some embodiments, multiple viral or virally-derived proteins are expressed under the control of the same type of promoter. In some embodiments, multiple viral or virally-derived proteins are expressed behind the same promoter. In some embodiments, multiple viral or virally-derived proteins are expressed from different vectors. In some embodiments, multiple viral or virally-derived proteins are expressed under the control of different types of promoters.

Embodiments described herein are not limited by the identity of the vector(s). Expression vectors may include: a regulatory sequences for protein expression such as promoter, enhancer, a terminator; a replication origin; and a selection marker such as URA3, LEU2, HIS3, TRP1, LYS2, etc.

Proteins

In some embodiments, VLPs (e.g., eVLPs) comprising viral (e.g., Influenza, HIV, Ebola, etc.) proteins are provided. In some embodiments, VLPs (e.g., eVLPs) comprising virally-derived proteins (e.g., natural viral proteins, synthetic mutant viral proteins, viral fusion proteins, structural or functional equivalents, etc.) are provided. In some embodiments, methods of expression such proteins and generating VLPs therefrom are provided.

In some embodiments, compositions provided herein comprise proteins from the virus families: Hepadnaviridae (e.g., Hepatitis B virus, etc.), Herpesviridae (e.g., Herpes simplex virus, varicella-zoster virus, cytomegalovirus, Epstein-Barr virus, etc.), Togaviridae (e.g., Rubella virus, alphavirus, etc.), Arenaviridae (e.g., Lymphocytic choriomeningitis virus), Flaviviridae (e.g., Dengue virus, hepatitis C virus, yellow fever virus, etc.), Orthomyxoviridae (e.g., Influenzavirus A, influenzavirus B, influenzavirus C, isavirus, thogotovirus, etc.), Paramyxoviridae (e.g., Measles virus, mumps virus, respiratory syncytial virus, Rinderpest virus, canine distemper virus, etc.), Bunyaviridae (e.g., California encephalitis virus, hantavirus, etc.), Rhabdoviridae (e.g., Rabies virus, etc.), Filoviridae (e.g., Ebola virus, Marburg virus, etc.), Coronaviridae (e.g., Corona virus, etc.), Bornaviridae (e.g., Borna disease virus, etc.), Arteriviridae (e.g., Arterivirus, equine arteritis virus, etc.), Retroviridae (e.g. human immunodeficiency virus (HIV), etc.), etc. In some embodiments, compositions provided herein comprise proteins derived from the aforementions families (e.g., mutants thereof, fusions thereof, chimeras thereof, etc.).

Structural

In some embodiments, VLPs (e.g., eVLPs) comprise at least one structural viral protein (or structural virally-derived protein). In some embodiments, the structural protein is an internal structural protein. In some embodiments, any structural protein capable of initiating or otherwise being involved in the budding of a VLP (e.g., eVLP) from a spheroplast finds use in embodiments described herein. In some embodiments, the identity of the structural protein(s) dictates or greatly influences the shape (e.g., filamentous, spherical, icosahedral, etc.) of the resulting eVLP. In some embodiments, this structural protein forms the matrix layer (or other structural layer underlying the envelope) or matrix-like portion of the VLP (e.g., the protein layer underlying the envelope). In some embodiments, the structural protein is a matrix protein (or matrix-like protein). In some embodiments, two or more matrix proteins (or matrix-like proteins)

are provided. In some embodiments, additional non-matrix structural proteins are provided (e.g., surface-displayed proteins, core proteins, capsid proteins, etc.

In some embodiments, upon expression within a yeast or other suitable expression system (e.g., above a threshold level), the internal structural protein (e.g., matrix or matrix-like protein) populates beneath the yeast (or other) plasma membrane and forms an internal structural layer (e.g., matrix-like layer). In some embodiments, interactions between structural (e.g., matrix) proteins allow for assembly of the matrix layer. In some embodiments, upon degradation of the yeast cell wall (or analogous layer), the matrix-like layer and plasma membrane bud off of the spheroplast to form eVLPs. In some embodiments, upon degradation of the yeast cell wall: (1) the matrix or matrix-like protein populates beneath the yeast plasma membrane and forms a matrix-like layer, and (2) the matrix-like layer and plasma membrane bud off of the spheroplast to for eVLPs.

Surface

In some embodiments, VLPs described herein display one or more surface-displayed, integral membrane, and/or transmembrane proteins. In some embodiments, one or more surface-displayed, integral membrane, and/or transmembrane proteins are expressed in a system described herein (e.g., within a yeast cell) and attach to the biological membrane of the system (e.g., yeast plasma membrane) according to the protein's particular affinity for membranes. In some embodiments, upon spheroplast formation and budding of the VLP from the expression system, the surface-displayed, integral membrane, and/or transmembrane proteins are located on, across, or within the envelope of the VLP. Viral surface proteins are also known as "spikes." These spikes play essential roles in viral biology, including, but not limited to: viral budding, cellular recognition, attachment to host cell, evading recognition by host immune systems, etc. In some embodiments, surface-displayed proteins are targets for viral-recognition by the host subject's immunologic defenses (e.g., antibodies, B cells, T cells, etc.). Surface proteins are also the targets for many antiviral agents and/or immunotherapies. Due to the importance of viral surface proteins in viral biology as well as natural and medical defenses against viral infection, the presence of surface-displayed viral or virally-derived proteins is an essential feature of certain embodiments described herein.

In some embodiments, transmembrane or other surface-displayed proteins are glycoproteins. Glycoproteins are proteins that contain oligosaccharide chains (glycans) covalently attached to polypeptide side-chains, via a cotranslational or posttranslational process known as glycosylation. In some embodiments, expression systems (e.g., yeast cells) that find use herein are capable of providing properly glycosylated glycoproteins and locating them at the plasma membrane. In some embodiments, glycoproteins produced in the expression systems describe herein bud off of spheroplasts with the VLPs and are displayed on the VLP surface. Exemplary glycoproteins include HA and NA from Influenza, GP from Ebola, and GP120 and GP41 from HIV. In some embodiments, virally-derived glycoproteins (e.g., synthetic variant of natural glycoproteins, fragments of natural glycoproteins, fusions of glycoproteins with other peptides or polypeptide, chimeras of different glycoproteins, etc.) are expressed in the expression systems described herein and displayed on or within the VLP envelope.

In some embodiments, surface-displayed proteins are transmembrane proteins that are embedded within the VLP envelope. In some embodiments, such transmembrane proteins have a surface displayed portion. In some embodiments, surface-displayed proteins are surface proteins that are linked to the exterior of the VLP envelope and/or to a transmembrane protein (e.g., GP41 is linked to GP120). In some embodiments, surface proteins are expressed within the expression systems described herein, and present on the VLPs upon budding. In some embodiments, surface proteins are added after VLP budding an attach or embed with the envelope.

Other

Proteins expressed in the systems and methods described herein and contained on or within the VLPs described herein are not limited to surface proteins and/or the structural proteins the enable formation of the VLPs. In some embodiments, other viral proteins, virally-derived proteins (e.g., capsid, core, viral enzymes, etc.), or non-viral proteins (e.g., therapeutics proteins or peptide, fluorescent or other marker proteins, etc.) are displayed on or contained within the VLPs. In some embodiments, these other proteins, which may or may not play a role in the VLP assembly, have functional roles associate with the particular intended application of the VLP (e.g., vaccine, immunotherapy, research carrier, etc.).

Lipid Membrane

In some embodiments, an eVLP is generated by expression of viral proteins within a yeast cell (or other expression system), and then budded from the yeast lipid membrane following removal of the yeast cell wall. As a consequence of this technique, in some embodiments, eVLPS produced in some systems described herein and/or using the methods described herein are enveloped in yeast-derived lipid membranes. Therefore, the eVLPs described in some embodiments herein have envelopes that approximate the composition of a yeast lipid membrane. The composition of a yeast lipid membrane is well understood in the field and described, for example, in Van der Rest et al. MICROBIOLOGICAL REVIEWS, June 1995, p. 304-322; herein incorporated by reference in its entirety. In some embodiments, this includes a lipid composition of one or more (e.g., all) of: 5-25% phosphatidylcholine (e.g., 5%, 10%, 15%, 20%, 25%, and any ranges therein), 5-25% phosphatidylethanolamine (e.g., 5%, 10%, 15%, 20%, 25%, and any ranges therein), 10-35% phosphatidylinositol (e.g., 10%, 15%, 20%, 25%, 30%, 35%, and any ranges therein), 0-40% phosphatidylserine (e.g., 0%, 5%, 10%, 15%, 20%, 25%, 30%, 35%, 40%, and any ranges therein), 0-10% cardiolipin (e.g., 0%, 2%, 4%, 6%, 8%, 10%, and ranges therein), 0-10% phosphatidic acid (e.g., 0%, 2%, 4%, 6%, 8%, 10%, and ranges therein), 10-50% sphingolipids (e.g., 0%, 5%, 10%, 15%, 20%, 25%, 30%, 35%, 40%, 45%, 50%, and any ranges therein), and/or 0-15% other lipids (e.g., 0%, 5%, 10%, 15%, and ranges therein). In some embodiments, this includes a fatty acid (length and saturation) composition of one or more (e.g., all) of: 0-15% 10-14:1 (e.g., 0%, 5%, 10%, 15%, or ranges therein), 5-20% 16:0 (e.g., 0%, 5%, 10%, 15%, 20%, or ranges therein), 20-40% 16:1 (e.g., 20%, 25%, 30%, 35%, 40%, or ranges therein), 5-15% 18:0 (e.g., 5%, 10%, 15%, or ranges therein), 20-40% 18:1 (e.g., 20%, 25%, 30%, 35%, 40%), 0-10% 18:3 (e.g., 0%, 5%, 10%, or ranges therein), 5-15% 20-24 (e.g., 5%, 10%, 15%, or ranges therein), etc.

In some embodiments, eVLP-production cells or systems comprise other lipid and/or fatty acid compositions. In some embodiments, eVLP-production cells or systems comprise other membrane components (e.g., sterols (e.g., cholesterol, campesterol, sitosterol, stigmasterol, ergosterol, etc.), lipids, fatty acids, etc.) in any suitable concentrations. In some embodiments, eVLP-production cells or systems are supplemented with additional components in order to produce a desirable envelope for a particular eVLP (e.g., particular application, particular virus type, particular size, particular shape, etc.). For example, in some embodiments, cryopreservatives or cryoprotective agents are added to the membrane. In some embodiments, eVLPs are supplemented with additional components after budding from the spheroplasts in order to produce a desirable envelope for a particular eVLP (e.g., particular application, particular virus type, particular size, particular shape, etc.).

Cell Wall Disruption

In some embodiments, the budding of VLPs (e.g., eVLPs) is induced by the formation of spheroplasts (or other non-cell-walled bodies) from yeast cells or other cellular or non-cellular expression systems. In some embodiments, cell wall is removed or compromised by mechanical rupture, chemical degradation/destabilization, enzymatic digestion/degradation, or any suitable combinations thereof. In some embodiments, a cell wall (e.g., yeast cell wall) is completely or partially (e.g., >50%, >75%, >90%) removed or degraded by the administration of a cell wall digestion enzyme, such as Zymolase or Lyticase. Any other suitable techniques for the creating or spheroplasts or other similar bodies may find use in embodiments described herein.

Influenza eVLPs

The influenza virus is an enveloped virus and belongs to the orthomyxoviridae. It has three types, A, B and C. The viral envelope is decorated by two viral glycoproteins HA and NA and there are 18 different HA and nine different NA antigens. The influenza A virus is subtyped based on the HA and NA antigens as H1N1, H3N2, etc. Annual vaccination is recommended to control the influenza virus infection (flu). Traditional flu vaccine contains two strains of influenza A (H1N1, H3N2) and one strain of influenza B. Each strain of influenza virus is individually grown in fertilized chicken eggs and processed for manufacture of the vaccine. The influenza strains are inactivated and combined to produce the trivalent vaccine. Influenza virus has a very high mutation rate and each year a new strain of influenza virus could emerge which is antigenically different from the parent strains. Thus, the influenza vaccine provides good protection against the incorporated strains but is less effective against the emerging flu strains. Therefore, the flu vaccine formulation is revised each year to incorporate the prevalent strain of influenza virus, and the vaccine does not provide life-long immunity against the flu. Thus, a vaccine is needed that (1) incorporates more influenza strains to provide a border protection against flu, (2) provides longer lasting viral immunity (e.g., >1 year, >2 years, >5 years, >10 years, >15 years, >20 years, etc.), (3) is coupled with antigens for other viruses to reduce the number of immunizations a subject needs, and/or (4) provides more potent immunity to influenza infection.

Experiments were conducted during development of embodiments described herein to produce of influenza VLPs, and systems and methods of production thereof. The approach used to generate the influenza VLPS described herein uses a yeast system to produce antigenic and non-infectious VLPs that can, for example, be used in a vaccine against the flu. The yeast system is efficient at producing viral proteins and glycoproteins and multiple different proteins (e.g., M1, M2, NA, HA, etc.) can be expressed and produced in sufficient quantity in yeast cells. Furthermore, because the yeast cells efficiently recombine multiple gene fragments via homologous recombination less time is need to expressed genes of interest in yeast cells compared to, for example, insect cells.

The viral glycoprotein HA is mainly responsible for virus attachment to cells and infection. Therefore, antibodies generated against the HA are important for the virus neutralization. In experiments conducted during development of embodiments of the present invention, viral HA, NA, M1 and M2 proteins have been overexpressed in yeast cells using, for example, galactose inducible promoters to form the virus-like particles. These proteins assemble on the yeast plasma membrane and forming the virus-like particles within the yeast cell. The VLPs are released following removal of the yeast cell wall and continue to form and bud from the yeast spheroplasts following culture of the spheroplasts in an environment that maintains their integrity.

In some embodiments, an Influenza structural protein (e.g., M1 and/or M2), or a variant derived therefrom is expressed in cells or a system (e.g., yeast cells) that allows for assembly of Influenza eVLPs according to the systems and methods described herein. In some embodiments, an Influenza VLP further comprises one or more Influenza surface proteins (e.g., NA and/or HA). In some embodiments, an Influenza eVLP comprise one or both of M1 and M2 and one or both of Ha and NA. In some embodiments, an Influenza VLP comprises multiple variants of HA (e.g., H1, H2, H3, H4, H5, H6, H7, H8, H9, H10, H11, H12, H13, H14, H15, H16, H17, and/or H18) and/or NA (e.g., N1, N2, N3, N4, N5, N6, N7, N8, and/or N9). In some embodiments, an Influenza VLP comprises Ha and/or NA, but one or more structural proteins from (or derived from) another virus or a generic (e.g., synthetic) VLP structural protein. In some embodiments, Influenza VLPs comprise M1, M2, one or more HA types, and one or more NA types. In some embodiments, an Influenza VLP further comprises additional Influenza proteins, such as nucleoprotein (NP), NS1, NS2 (NEP: nuclear export protein), PA, PB1 (polymerase basic 1), PB1-F2 and/or PB2. In some embodiments, Influenza eVLPs are produced comprising one or more (e.g., two or more, 3, 4, 5, 6, 7, 8, 9, 10, 11) of M1, M2, NA, HA, NP, NS1, NS2, PA, PB1, PB1-F2, and/or PB2. Influenza eVLPs are not limited to naturally occurring Influenza protein sequences. Rather, variant Influenza proteins (e.g., comprising truncations, internal deletions, substitutions, additions, fusions with other proteins or peptides, etc.) may be utilized in order to enhance: antigenic activity, efficiency of VLP assembly, expression, compatibility with human administration, etc.

Ebola eVLPs

Ebola virus (EBOV, formerly designated Zaire ebolavirus) is one of five known viruses within the genus Ebolavirus. Four of the five known ebolaviruses, including EBOV, cause a severe and often fatal hemorrhagic fever in humans and other mammals, known as Ebola virus disease (EVD). Ebola virus has caused the majority of human deaths from EVD, and is the cause of the 2013-2015 Ebola virus epidemic in West Africa, which has resulted in at least 23,860 suspected cases and 9,675 confirmed deaths. The EBOV genome is a single-stranded RNA approximately 19,000 nucleotides long. It encodes seven structural proteins: nucleoprotein (NP), polymerase cofactor (VP35), (VP40), GP, transcription activator (VP30), VP24, and RNA-dependent RNA polymerase (L). Ebola virions are cylindrical/tubular and comprise a viral envelope (e.g., lipid membrane), matrix, and nucleocapsid components. The overall cylinders are generally approximately 80 nm in diameter, and have a virally encoded glycoprotein (GP) projecting as 7-10 nm long spikes from its lipid bilayer surface. The cylinders are of variable length, typically 800 nm, but sometimes up to 1000 nm long. The outer viral envelope of the virion is derived by budding from domains of host cell membrane into which the GP spikes have been inserted during their biosynthesis. Individual GP molecules appear with spacings of about 10 nm.

It has been demonstrated that Ebola virus VP40 (e.g., Ebola matrix protein) drives the formation of virus-like filamentous particles along with GP (e.g., Ebola glycoprotein) (See, e.g., Noda et al. J Virol. 2002 May; 76(10):4855-65; herein incorporated by reference in its entirety). In some embodiments, VP40 and GP are expressed in cells or a system (e.g., yeast cells) that allow for assembly of Ebola eVLPs according to the systems and methods described herein. In some embodiments, additional Ebola proteins, such as NP (nucleoprotein), VP35, VP30, and/or VP24, are further expressed. In some embodiments, Ebola eVLPs are produced comprising one or more (e.g., two or more, 3, 4, 5, or 6) of VP24, VP30, VP35, VP40, NP, and GP. In some embodiments, Ebola eVLPs comprise VP24, VP40, and GP. In some embodiments, Ebola eVLPs comprise VP40 and GP. In some embodiments, Ebola eVLPs comprise VP40. In some embodiments, additional Ebola proteins or non-Ebola proteins (e.g., proteins of another virus) are also expressed. Experimental work indicates that mutation of Ebola proteins GP, NP, VP40 and/or VP24 account for different clinical outcomes during natural human Ebola infection and that mutations in any of these proteins can influence virulence (Leroy et al. J Gen Virol January 2002 vol. 83 no. 1 67-73; herein incorporated by reference in its entirety). Therefore, in some embodiments, eVLPs are produced comprising one or more (e.g., 2, 3, or 4) of GP, NP, VP40 and VP24. Ebola eVLPs are not limited to naturally occurring Ebola protein sequences. Rather, variant Ebola proteins (e.g., comprising truncations, internal deletions, substitutions, additions, fusions with other proteins or peptides, etc.) may be utilized in order to enhance: antigenic activity, efficiency of VLP assembly, expression, compatibility with human administration, etc.

In some embodiments, Ebola eVLPS adopt cylindrical (or filamentous) morphology, similar to the naturally occurring virions. In some embodiments, the shape of the Ebola eVLP is driven by the identity of the Ebola proteins comprising it. In some embodiments, an eVLP comprising (e.g., wherein the majority of the protein content (e.g., >50%, >60%, >70%, >80%, >90%, >95%, >99%) comprises) VP40; VP40 and GP; or VP40, VP24, and GP will adopt a cylindrical (or filamentous) morphology (e.g., resembling or mimicking the Ebola virion morphology). In some embodiments, eVLP cylinders are between 15 and 160 nm in diameter (e.g., about 15 nm, 20 nm, 30 nm, 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, and any ranges therein) and/or 400 to 4000 nm in length (e.g., about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, about 2000 nm, about 2500 nm, about 3000 nm, about 3500 nm, about 4000 nm, and any ranges therein).

In some embodiments, Ebola eVLPS (e.g., capable of producing an antigenic response) are not limited to cylindrical (or filamentous) morphology or other Ebola-virion-like characteristics (e.g., GP spacing, size, etc.). In some embodiments, Ebola eVLPs are spherical or any other suitable shape. In some embodiments, eVLp shape is dictated by the cell or system within which they are produced and/or other factors instead of or in addition to eVLP protein identity.

HIV eVLPs

The human immunodeficiency virus (HIV) is a lentivirus (a subgroup of retrovirus) that causes the acquired immunodeficiency syndrome (AIDS), a condition in humans in which progressive failure of the immune system allows life-threatening opportunistic infections and cancers to thrive.

The RNA genome of HIV contains of nine genes (gag, pol, and env, tat, rev, nef, vif, vpr, vpu), encoding 19 proteins. Of these the Gag protein is processed to form the proteins that provide the basic physical infrastructure of the virus: p17 (matrix (MA)), p24 (capsid (CA)), p2 (spacer 1 (SP1), p7 (nucleocapsid (NC), p1 (spacer 2 (SP2)), and p6, The env gene produces a glycoprotein (GP160) that is processed to produce glycoproteins GP120 (surface (SU)) and GP41 (Transmembrane™) which are together displayed on the exterior of the viral envelope.

Although it has been demonstrated that particles can be produced comprising only unprocessed Gag protein (U.S. Pat. Pub. 2004/0009193 to Morikawa et al.; herein incorporated by reference in its entirety), such particles lack many of the structural and antigenic features of the HIV eVLPs (and other eVLPS) described herein. For example, the surface-displayed GP120 and GP41, which provide major antigenic determinants of HIV, as absent in the Morikowa work. Therefore, the Gag proteins in those particles are completely encapsulated in the yeast membrane, and likely not available, for example, for recognition by a host immune system.

In some embodiments, provided herein are HIV eVLPs, and methods and systems (e.g., synthetic yeast cells) for the production thereof, comprising two or more of HIV proteins: unprocessed Gag (e.g., uncleaved), MA, CA, SP1, NC, SP2, p6, GP160, GP120, and GP41. In some embodiments, HIV eVLPs comprise (1) Gag and (2) GP160, GP120, and/or GP41. In some embodiments, HIV eVLPs comprise (1) MA and (2) GP160, GP120, and/or GP41. HIV eVLPs are not limited to naturally occurring HIV protein sequences. Rather, variant HIV proteins (e.g., comprising truncations, internal deletions, substitutions, additions, fusions with other proteins or peptides, etc.) may be utilized in order to enhance: antigenic activity, efficiency of VLP assembly, expression, compatibility with human administration, etc.

In some embodiments, HIV eVLPS adopt an approximately spherical morphology, similar to the naturally occurring virions. In some embodiments, the shape of the HIV eVLP is driven by the identity of the HIV proteins comprising it. In some embodiments, an eVLP comprising (e.g., wherein the majority of the protein content (e.g., >50%, >60%, >70%, >80%, >90%, >95%, >99%) comprises, for example: MA; Gag; (1) MA or Gag, and (2) GP160, GP120, and/or GP41 will adopt a spherical morphology (e.g., resembling or mimicking the HIV virion morphology). In some embodiments, eVLP spheres are between 60 and 240 nm in diameter (e.g., about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, and any ranges therein)

In some embodiments, HIV eVLPS (e.g., capable of producing an antigenic response) are not limited to spherical morphology or other HIV-like characteristics (e.g., GP120/GP41 spacing, size, etc.). In some embodiments, HIV eVLPs are cylindrical, polygonal, or any other suitable shape. In some embodiments, HIV eVLP shape is dictated by the cell or system within which they are produced and/or other factors instead of or in addition to eVLP protein identity.

Other eVLPs

Numerous diseases are understood to be caused by enveloped viruses. In some embodiments, with an understanding of the structural and/or surface-displayed components of such viruses, eVLPs that elicit an antigenic response are produced. In some embodiments, the systems and methods described herein allow for the production of multiprotein eVLPS displaying surface proteins for any suitable enveloped virus for which the structural and/or surface-displayed components (e.g., proteins and glycoproteins) are known or can be identified. Examples of other viruses, and their structural and surface protein components, that find use in such embodiments are provided below (Table 1).

TABLE 1

Exemplary components for production of eVLPs

| Virus | Structural Protein(s) | Surface Protein(s) |
|---|---|---|
| Measles virus | M (Matrix) | HN (Haemagglutinin-Neuraminidase), F (Fusion) |
| Rabies virus | M (Matrix) | G (Glycoprotein) |
| Hepatitis B virus | Icosahedral core (HBcAg) | Surface antigen (HBsAg) |
| Herpes simplex virus | Tegument protein | Glycoproteins gB, gC, gD, gH and/gL |
| Coronavirus | Membrane protein | Spike glycoprotein |
| Dengue fever virus | Nucleocapsid | Envelop glycoproteins |
| Yellow Fever virus | Nucleocapsid | Envelope glycoproteins |

Virally-Chimeric eVLPs

Embodiments are not limited to eVLPs comprising protein from, or variants derived from, a single virus type or strain. In some embodiments, an eVLP comprises proteins from two or more strains or types of the same virus (e.g., Influenza A and B; two or more of H1N1, H5N3, H3N2, etc.; HIV-1 and HIV-2; two or more viruses of the genus Ebolavirus;

etc.). In some embodiments, an eVLP comprises proteins from (or derived from) two or more different viruses (e.g., selected from HIV, Influenza, Ebola, Hepatitis B virus; Herpes simplex; etc.). In some embodiments, an eVLP comprises a matrix protein (or other internal structural protein) from (or derived from) a first virus (e.g., first type or strain) and surface-displayed proteins (e.g., glycoproteins) from (or derived from) two or more viruses (e.g., the first virus and one or more others, a second virus and one or more others, etc.). In some embodiments, an eVLP comprises a generic internal structural (e.g., matrix or matrix-like) protein (or other internal structural protein) derived from one or more viral proteins or designed and surface-displayed proteins (e.g., glycoproteins) from two or more viruses. In some embodiments, a generic internal structural (e.g., matrix or matrix-like) protein or set of generic proteins along with the systems and methods described herein provides a platform for the generation of eVLPs displaying any suitable surface proteins and/or glycoproteins from any number (e.g., 1, 2, 3, 4, 5, 6, 7, 8, 9, 10, or more) or viruses or strains.

Applications

Vaccines

In some embodiments, VLPs are a useful as vaccines or as a tool for the development of vaccines. In some embodiments, VLPs contain high-density display of viral surface proteins and/or glycoproteins which present conformational viral epitopes that can elicit strong T cell and B cell immune responses (Akahata W, Yang Z Y, Andersen H, et al. Nature Medicine (2010) 16 (3): 334-8; herein incorporated by reference in its entirety). Additionally, since VLPs typically lack viral genetic material, they provide a safer alternative to live attenuated viruses. VLPs have already been used to develop FDA approved vaccines for Hepatitis B and human papillomavirus, and a pre-clinical vaccine against chikungunya virus.

Carriers

In some embodiments, the VLPs described herein are useful as carriers of therapeutics (e.g., small molecule drugs, gene therapy agents, peptides, etc.), imaging agents, etc. In some embodiments, VLP carriers are administered to a subject in order to deliver a payload within (e.g., encapsulated with the envelope and/or matrix-like layer of the VLP), embedded within the membrane of, or attached to the VLP.

In some embodiments, VLPs are tuned to recognize and fuse with a particular type of target cell (e.g., based on the proteins displayed on the surface of the VLP) and to deliver a payload to such cells. In such embodiments, VLPs allow cell-type-specific deliver of a molecular payload.

In some embodiments, VLPs are not limited by the type of payload they deliver. For example, suitable payloads include nucleic acids (e.g., for transfection or transformation, siRNA, miRNA, antisense RNA, CRISPR/Cas9 genome editing (e.g., cell-type-specific genome editing), etc.), peptides/polypeptides/proteins, small molecule (e.g., drug, toxin, ligand, etc.), etc.

Research

In some embodiments, the VLPs described herein find use in viral research. Since the VLPs are non-infective, in some embodiments, they are used to study aspects of viral structure and function without the need for the safety requirements that may be necessary for research with infective viruses. Further, in some embodiments, VLPs find use in other research areas, such as the development of carriers, immunology, and the study of lipid membranes, transmembrane or integral membrane proteins, and trafficking across lipid membranes. In some embodiments, the VLPs described herein find use is testing various agents and components for use in eliciting an immune response. For example, drugs, antibodies, or other agents can be tested, using VLPs described herein, for the capacity to target the natural virus. Also VLPs find use in testing various combinations of antigens (e.g., on virally-derived surface proteins) for use in vaccines.

Administration

In some embodiments, eVLPs are provided as a pharmaceutical composition, for example, in an acceptable carrier and formulated into a suitable dosage form according to administration modes. For example, for oral administration, the pharmaceutical composition may be presented as discrete units, for example, capsules or tablets; powders or granules; solutions, syrups or suspensions (edible foam or whip formulations in aqueous or non-aqueous liquids); or emulsions. For parenteral administration, the pharmaceutical composition may include aqueous and non-aqueous sterile injection solutions which may contain anti-oxidants, buffers, bacteriostats and solutes which render the formulation substantially isotonic with the blood of the intended recipient; and aqueous and non-aqueous sterile suspensions which may include suspending agents and thickening agents. Excipients available for use in injectable solutions include, for example, water, alcohol, polyols, glycerin, and vegetable oils. Such a composition may be presented in unit-dose (single dose) or multiple dose (several doses) containers, for example, sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical composition may include antiseptics, solubilizers, stabilizers, wetting agents, emulsifiers, sweeteners, colorants, odorants, salts, buffering agents, coating agents, or anti-oxidants.

Compositions may comprise, in addition to eVLPs described herein, a therapeutically active agent (e.g., drug), antibodies, other immunotherapeutic agents, etc.

VLP compositions may be formulated into dosage forms for use in humans or veterinary use. Compositions may be administered to humans or non-human animals such as non-human primates, rodents, canines, felines, bovines, equines, porcines, etc. VLPs may be administered alone or in combination with another treatment.

VLP compositions may be administered in a pharmaceutically effective amount in a single- or multiple-dose. The pharmaceutical composition may be administered via any of the common routes, as long as it is able to reach the desired tissue. Thus, the present composition may be administered via oral or parenteral (e.g., subcutaneous, intramuscular, intravenous, or intradermal administration) routes, and may be formulated into various dosage forms. In one embodiment, the formulation is an injectable preparation. Intravenous, subcutaneous, intradermal, intramuscular and dropping injectable preparations are possible.

Screening

In some embodiments, methods, compositions, and systems are provided for testing and/or determining the effectiveness of various VLPs described herein or produced by the systems and methods described herein. In some embodiments, screening systems and method are provided to assess VLP effectiveness in any variety of application. In some embodiments, cells, antibodies, animals (e.g., rodents, etc.) are provided for testing VLP capacity for: recognition by antibodies or host immune system components, inducing or enhancing an immune response, treating infection, preventing infection, etc.

EXPERIMENTAL

Example 1

Inducible Promoter System

A previous study has shown that yeast cells can be used to produce human immunodeficiency virus (HIV) like particles by expressing a single HIV Gag protein under a constitutive promotor (Sakuragi, Goto et al. Proc Natl Acad Sci USA, 2002, 99(12): 7956-7961; herein incorporated by reference in its entirety). Experiments were conducted during development of embodiments described herein to explore the use of yeast cells to produce more complex virus like particles (VLPs) comprising multiple proteins and/or surface-displayed glycoproteins, such as influenza and Ebola VLPs. As shown in FIG. 1A, the "constitutive" system reported by Morikawa group failed to co-express the HA and NA using the constitutive THD3 and TEF1 promoters, two of the strongest constitutive promoters reported in yeast; in contrast, the "inducible" system described in embodiments herein showed co-expression of both. Furthermore, as shown in FIG. 1B, the inducible system successfully co-expressed four influenza viral proteins, HA1 NA1, M1, and M2, which are important for the function and assembly of the influenza VLP.

Example 2

Producing Influenza VLPs

An exemplary procedure for production of influenza VLPs is depicted in FIG. 2. Influenza HA, NA, M1, and M2 proteins were cloned from H1N1 influenza virus into *S. cerevesiae* via homologous recombination. Protein expression was induced by galactose-containing media. The yeast cell wall was removed with the enzyme lyticase and VLP were isolated by ultracentrifugation after further incubation.

Figure 3:
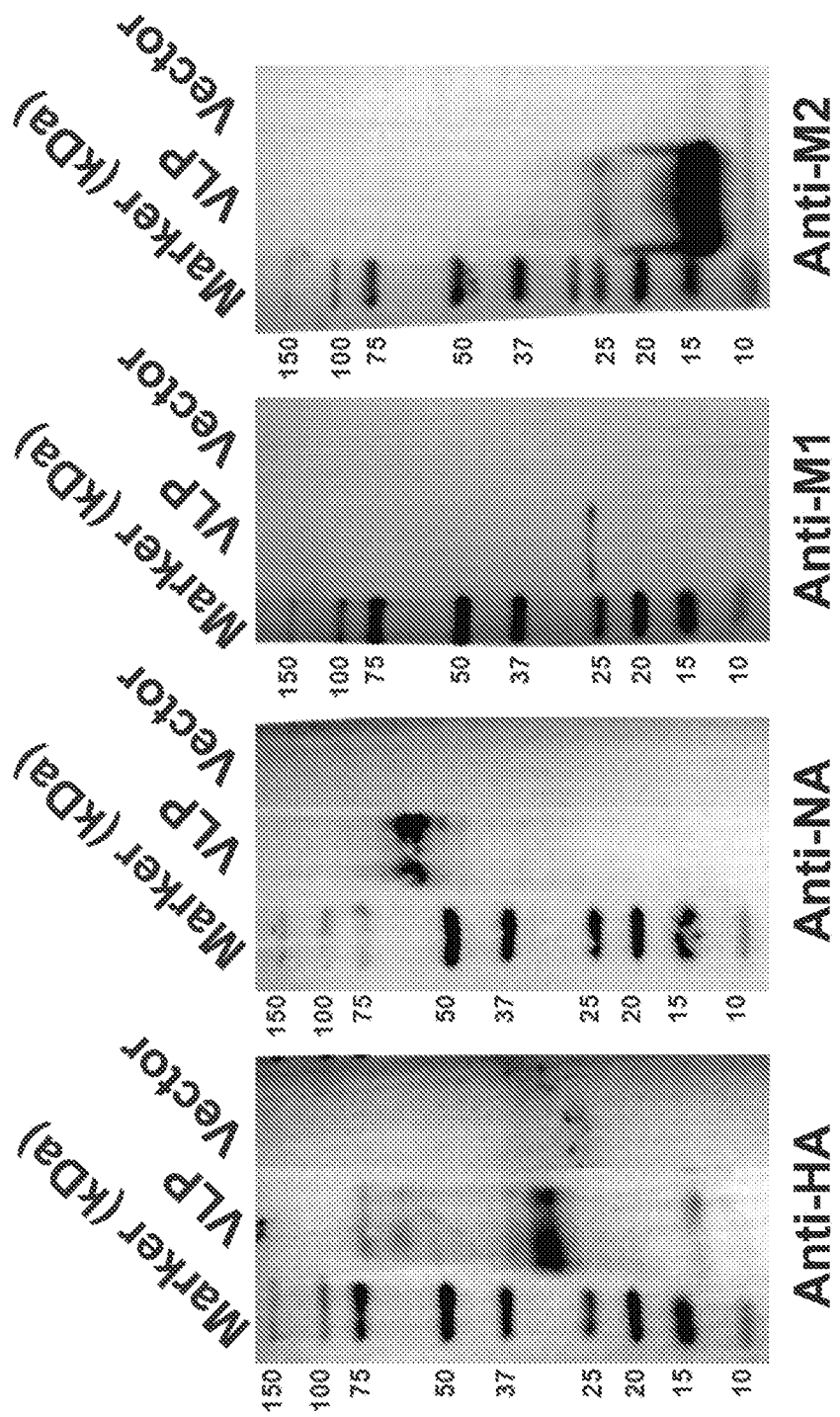
FIG. 3 shows a Western blot demonstration the expression of influenza proteins HA, NA, M1, and M2 in eVLPs produced in yeast.

The presence of influenza proteins was determined by Western blot analysis (FIG. 3). The HA, NA, M1, and M2 proteins were all clearly detected in clones containing the respective genes and not detected in control samples containing an empty vector.

Figure 4:
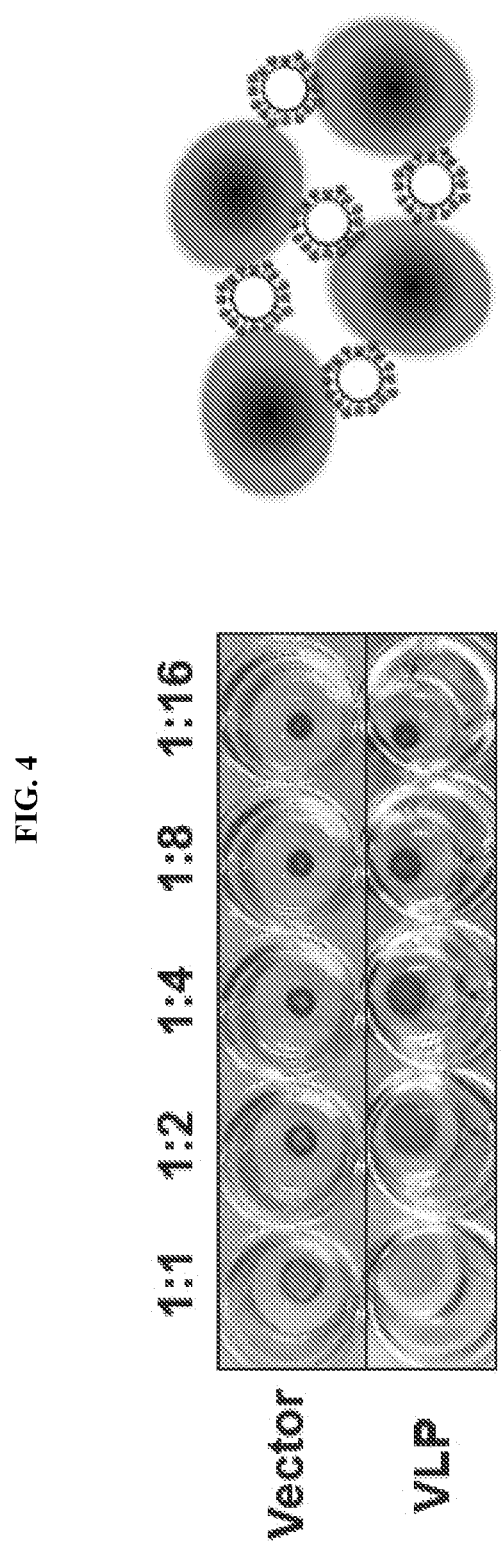
FIG. 4 shows a hemagglutination assay depicting the functionality of HA protein on eVLPs produced in yeast.

A hemagglutination assay was performed ascertain if the HA protein on the VLPs was functional (FIG. 4). The assay relies on the ability of functional HA to bind red blood cells (RBCs) into a polymeric network that prevents the RBCs from settling. The agglutination of VLP samples was greater than a control sample containing empty vector indicating that the HA protein is active and present on a particle.

Figure 5:
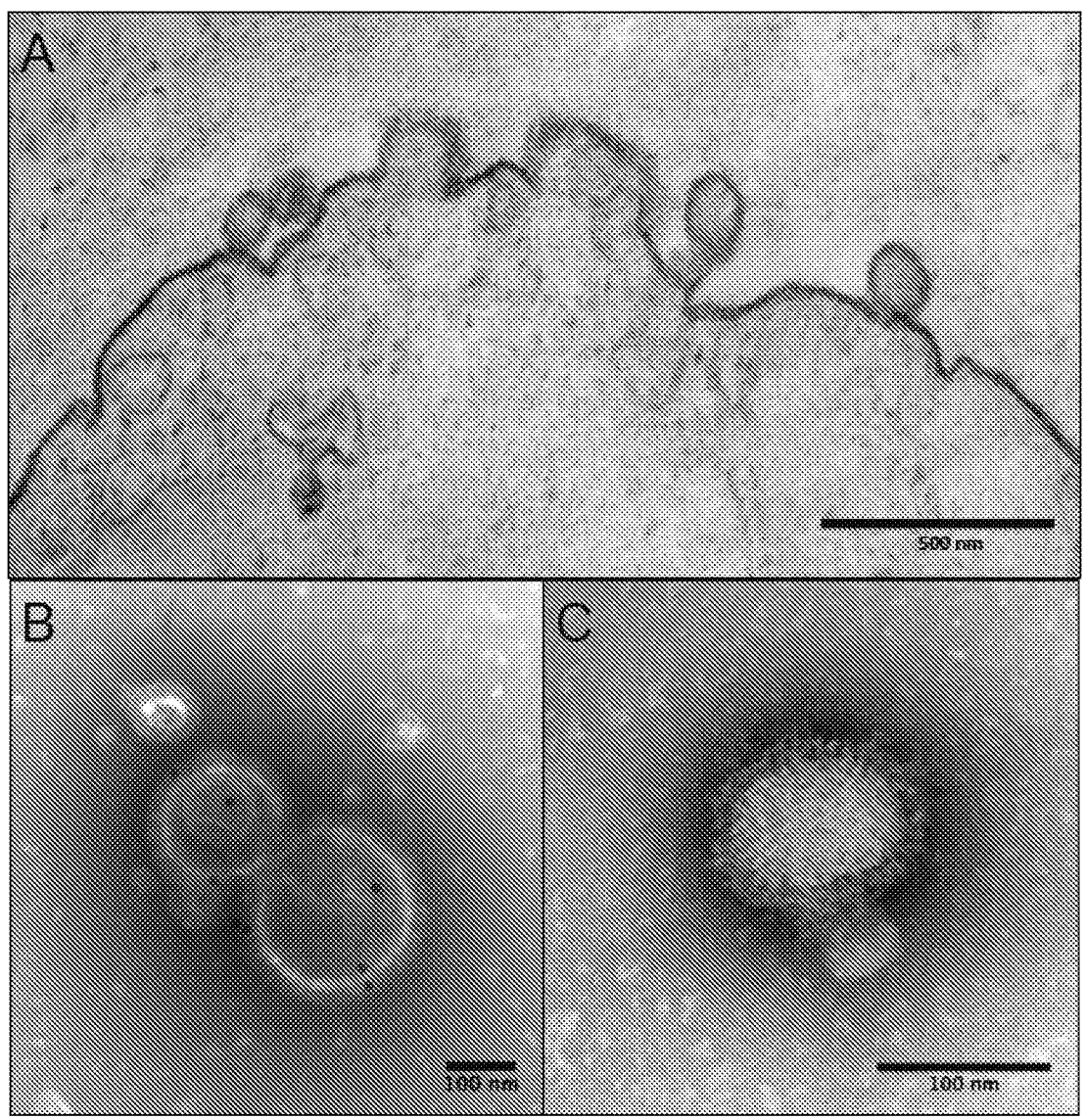
FIG. 5 shows transmission electron microscope imaging of (A) yeast cell after cell wall removal, (B) VLP immunolabeled with goldconjugated anti-M2 antibody, and (C) Influenza virus.

VLP morphology was confirmed by Transmission electron microscope imaging. Upon removal of the yeast cell wall, particles can be observed budding off of membrane and being released into medium (FIG. 5A). VLPs immunolabeled with gold-conjugated anti-M2 antibody demonstrate that the VLPs contain M2 protein and have signature HA "spikes" (FIG. 5B). The morphology and and presence of spikes appears similar between the VLPS and actual influenza virus (FIG. 5C).

Example 3

Producing Ebola VLPs

Figure 6:
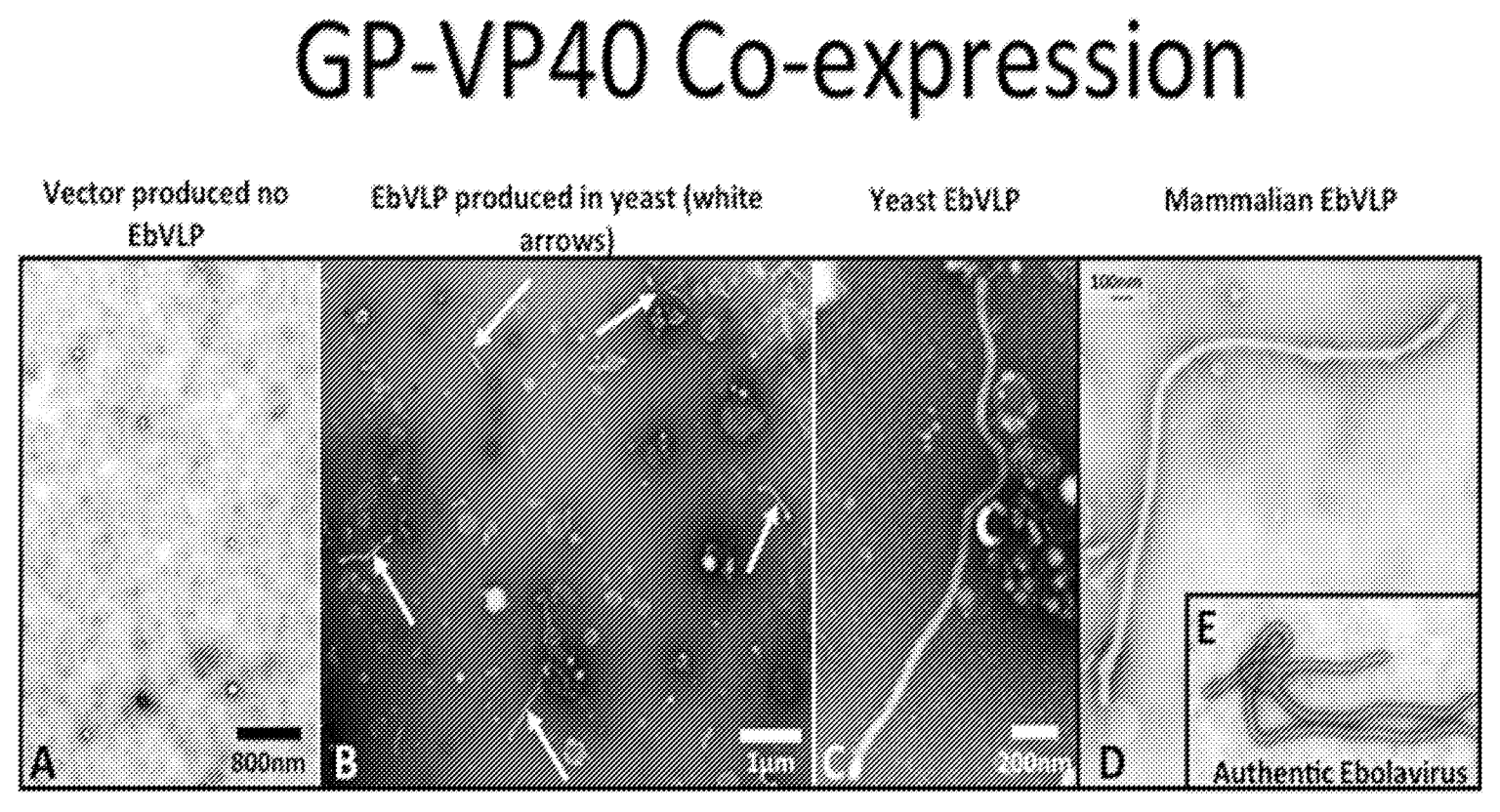
Figure 7:
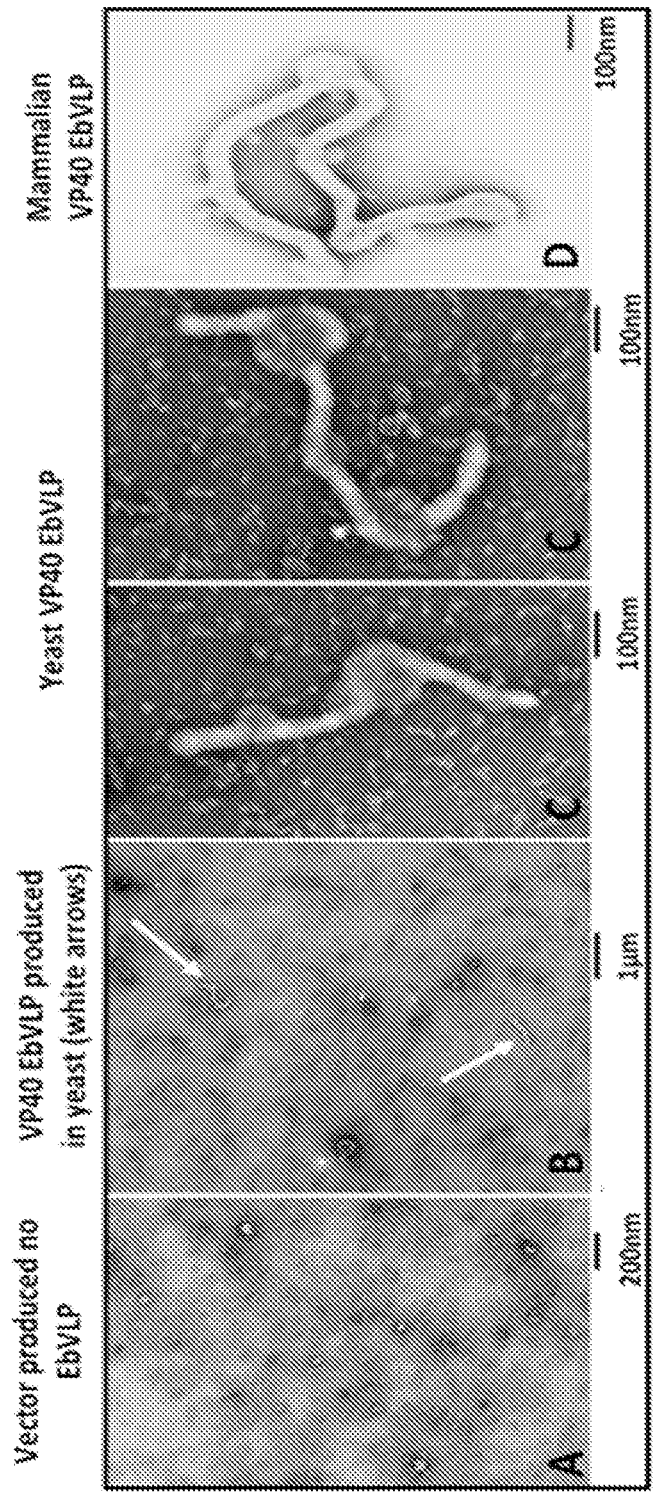
FIG. 7 shows transmission electron micrographs depicting EbVLPs produced by the expression Ebola protein VP40. Conformational similarity is observed between (C) yeast EbVLP and (D) mammalian EbVLP.
Figure 8:
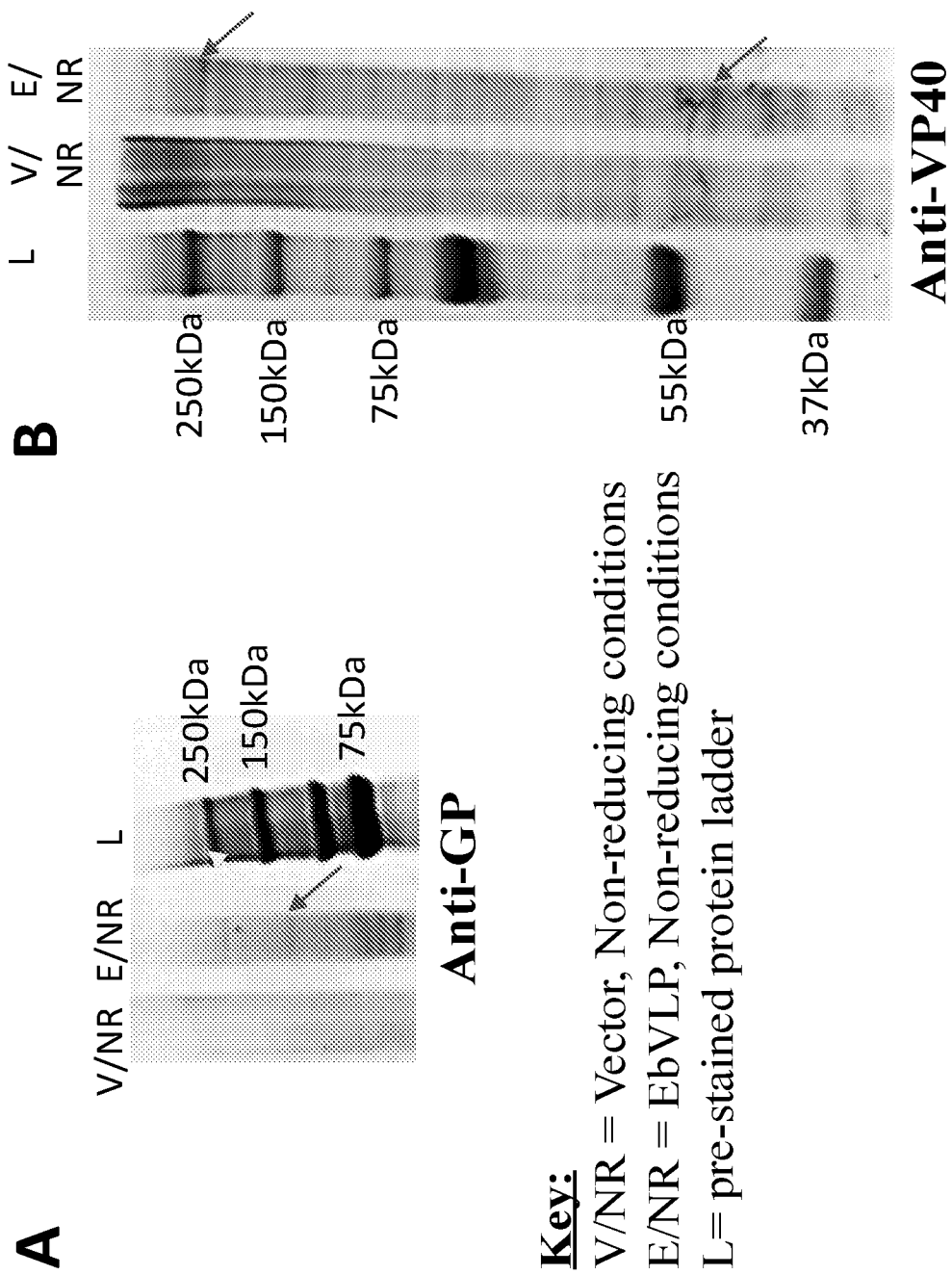
FIG. 8 shows Western blot analysis of Ebola eVLPs. (A) Staining with anti-GP antibody shows 150 kDa protein band under non reducing conditions in EbVLP sample not present in Vector. (B) Staining with anti-VP40 antibody shows ~250 kDa (hexamer) and ~45 kDa (monomer) band under non-reducing conditions in EbVLP, not present in Vector.

Experiments conducted during development of embodiments herein have demonstrated the synthesis of Ebola eVLPs (EbVLPs). EbVLPs were produced either by co-expression of Ebolavirus proteins GP and VP40 in yeast cells (FIG. 6) or expression of VP40 in yeast cells (FIG. 7), followed by processing using the methods described herein (i.e., expression was induced by galactose-containing media, yeast cell wall was removed by lyticase, and eVLP were isolated by ultracentrifugation). The resulting EbVLPs exhibited a filamentous shape, consistent with the morphology of Ebolavirus, and up to a few microns in length and about 20-100 nm in diameter. The EbVLPs comprise the expressed proteins (FIG. 8).

In addition to demonstrating the production of Ebola eVLPs using the methods described herein, these experiments demonstrate the capacity of the methods herein to produce eVLPs with a wide range of morphologies (e.g., spherical, filamentous), sizes, and compositions.

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

The invention claimed is:

1. An enveloped virus-like particle (eVLP) comprising:
   (a) a virally-derived internal structural protein;
   (b) a virally-derived surface-displayed protein; and
   (c) a yeast-plasma-membrane-derived envelope;
wherein the virally-derived surface-displayed protein is a transmembrane protein and spans the entire thickness of the yeast-plasma-membrane-derived envelope, and wherein the eVLP has a diameter of 50-240 nm, and wherein the virally-derived surface-displayed protein is displayed on the exterior of the eVLP.

2. The eVLP of claim 1, wherein an assembly of a plurality of said virally-derived internal structural protein underlies the envelope.

3. The eVLP of claim 1, wherein the surface-displayed protein is a glycoprotein.

4. The eVLP of claim 1, wherein the virally-derived internal structural protein is an influenza-derived matrix protein selected from influenza M1 and/or M2, wherein the virally-derived surface-displayed protein is a influenza-derived surface-displayed protein selected from influenza HA and/or NA.

5. The influenza eVLP of claim 4, comprising influenza-derived matrix protein or influenza-derived surface-displayed protein from two or more influenza types and/or strains.

6. The eVLP of claim 4, further comprising one or more of influenza proteins: NP, NS1, NS2, PA, PB1, PB1-F2 and/or PB2.

7. The eVLP of claim 4, comprising one or more HA types selected from the group consisting of H1, H2, H3, H4, H5, H6, H7, H8, H9, H10, H11, H12, H13, H14, H15, H16, H17, and H18; and comprising one or more NA types selected from the group consisting of N1, N2, N3, N4, N5, N6, N7, N8, and N9.

8. The eVLP of claim 1, wherein the virally-derived internal structural protein is Ebola-derived internal structural protein VP40; wherein the virally-derived surface-displayed protein is Ebola-derived surface-displayed protein GP.

9. The eVLP of claim 8, further comprising one or more of VP24, VP30, VP35, and NP.

10. The eVLP of claim 1, wherein the virally-derived internal structural protein is an HIV-derived internal structural protein selected from Gag, MA; wherein the virally-derived surface-displayed protein comprises HIV protein GP41.

11. The eVLP of claim 10, further comprising one or more of CA, SP1, NC, SP2, and/or p6.

12. A system for the production of enveloped virus-like particles (eVLPs) comprising:
   (a) a yeast cell engineered to express:
      (i) a virally-derived internal structural protein, and
      (ii) a virally-derived surface-displayed transmembrane protein;
   (b) yeast culture media; and
   (c) a spheroplasting cell wall-digesting enzyme.

13. The system of claim 12, wherein the yeast cell is stably or transiently engineered to express the two or more viral proteins.

14. A method for the production of an enveloped virus-like particle (eVLP) comprising:
   (a) expressing (i) a virally-derived internal structural protein, and (ii) a virally-derived surface-displayed transmembrane protein in a yeast cell in yeast culture media;
   (b) exposing the yeast cell to conditions that result in degradation of the yeast cell wall to produce a spheroplast; and
   (c) allowing budding of an eVLP from the spheroplast.

15. The method of claim 14, further comprising:
   (d) purifying the eVLP from the yeast culture media.

16. The method of claim 14, wherein conditions that result in degradation of the yeast cell wall to produce a spheroplast are selected from enzymatic digestion, mechanical rupture, and chemical destabilization.

17. The method of claim 16, wherein the enzymatic digestion is performed by a spheroplasting cell wall-digesting enzyme is selected from Zymolase and Lyticase.

18. A method of immunizing a subject against a viral infection comprising administering to the subject an effective dose of an enveloped virus-like particle (eVLP) of claim 1.

19. The eVLP of claim 1, wherein the eVLP comprises a cylindrical morphology.

20. The eVLP of claim 1, wherein the eVLP comprises a spherical morphology.

* * * * *